United States Patent [19]
Lee

[11] Patent Number: 5,179,937
[45] Date of Patent: Jan. 19, 1993

[54] DISPOSABLE VAGINAL SPECULUM

[76] Inventor: Chenault D. Lee, P.O. Box 363, Wanniassa ACT 2903, Australia

[21] Appl. No.: 705,757

[22] Filed: May 28, 1991

Related U.S. Application Data

[63] Continuation-in-part of Ser. No. 570,039, Aug. 20, 1990, abandoned, which is a continuation of Ser. No. 499,042, Mar. 26, 1990, abandoned, which is a continuation of Ser. No. 337,303, Apr. 13, 1989, abandoned.

[51] Int. Cl.⁵ .............................................. A61B 1/32
[52] U.S. Cl. .................................................... 128/17
[58] Field of Search ............................ 128/17, 18, 20; 606/197, 198, 3

[56] References Cited

U.S. PATENT DOCUMENTS

| 3,575,163 | 4/1971 | Gasper | 128/17 |
| 3,716,047 | 2/1973 | Moore | 128/18 |

FOREIGN PATENT DOCUMENTS

| 113829 | 7/1876 | France | 128/17 |
| 963632 | 7/1950 | France | 128/17 |
| 8701695 | 2/1987 | France . | |

Primary Examiner—Mark Graham
Attorney, Agent, or Firm—Edwin D. Schindler

[57] ABSTRACT

A disposable speculum of synthetic plastics material for vaginal inspection is described. The speculum comprises two dilation blade members which are attached to each other and movable apart. One of the blades has an extended handle portion which is so constructed that the included angle between the handle and the dilation blade is not less than 100 degrees.

9 Claims, 4 Drawing Sheets

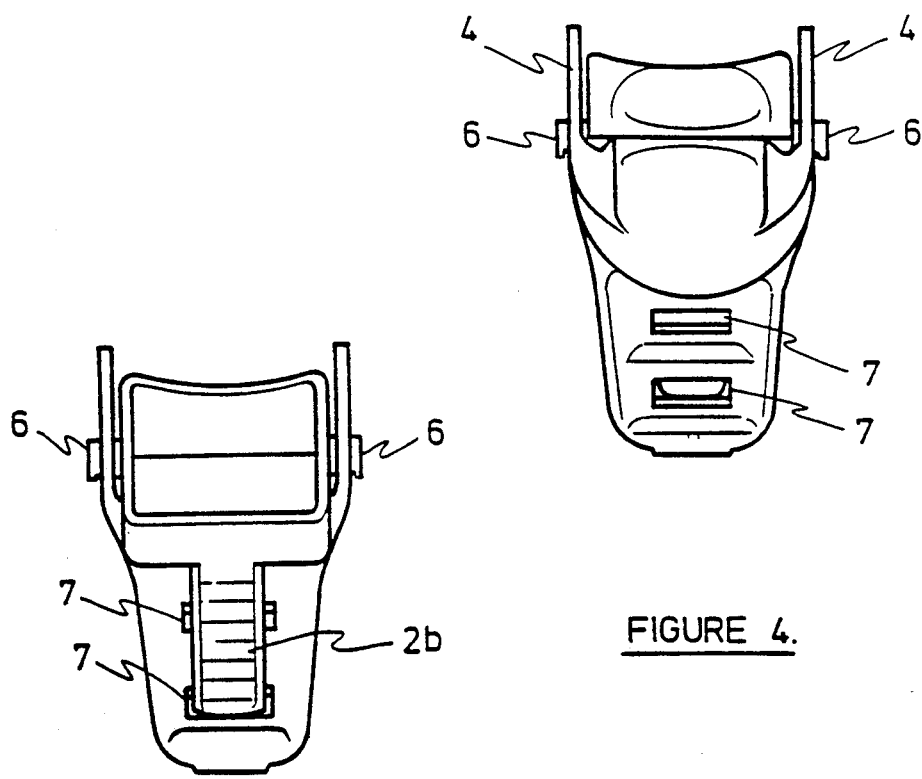
FIGURE 4.
FIGURE 5.
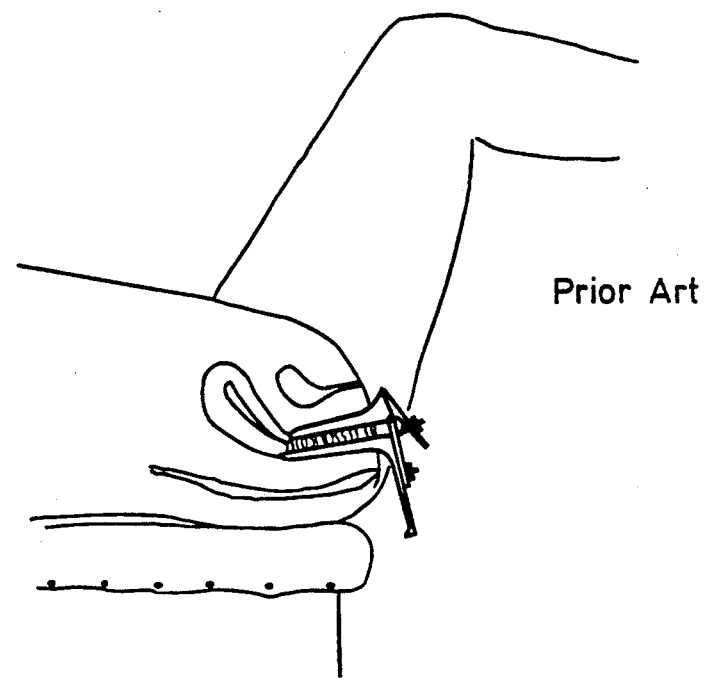
Prior Art
FIGURE 6.

DISPOSABLE VAGINAL SPECULUM

CROSS-REFERENCE TO RELATED APPLICATIONS

This is a continuation-in-part application of application Ser. No. 570,039, filed Aug. 20, 1990, now abandoned, which is a continuation of application Ser. No. 499,042, filed Mar. 26, 1990, now abandoned, which is a continuation of application Ser. No. 337,303, filed Apr. 13, 1989, now abandoned.

FIELD OF THE INVENTION

This invention relates to a speculum, and in particular to that type of speculum used for inspection of vaginal walls and the cervix uteri.

DESCRIPTION OF THE PRIOR ART

Prior art speculum construction has generally been of metal and comprised two elongate dilator blade portions which could be moved apart or together on a pivotal or lost motion type of hinge, the movement being performed by a pair of hand-grip sections which were extensions of the blade portions. One problem with the use of metal construction is the difficulty of sterilisation for reuse. This can only be properly done in an autoclave, and few general practitioners have such equipment available in their surgeries. Another problem is that metal feels cold and uncomfortable to the patient, so a metal speculum has to be warmed before use. In order to overcome these problems, it has been proposed to construct a cheap disposable speculum from a synthetic plastics material. These devices incorporate a slot and ratchet device as distinct from the metal constructed devices which use a thumb screw or the like, for the purpose of locking the blades of the speculum into a particular relative position.

However, the plastic disposable devices still suffer from the defects of unstable locking mechanism and unsuitability for use on patients lying on ordinary examination tables which are not constructed specifically for the purpose of gynaecological examinations.

A specific prior art instrument is shown in U.S. Pat. No. 3,332,414 to A D Gasper. This device, as well as all other bi-valve plastic speculums, suffers basic defects relative to the device of the present invention.

The vertical distance between the horizontal joint surfaces of the blades (24) (50) and the lowermost portion of the extended handle of the speculum makes it unsuitable for use on patients lying on an ordinary examination table. When a patient lies on an ordinary examination table which is flat, the back, buttocks and feet rest on the same table surface and the vagina is more or less parallel to, and approximately 8-10 cm above the surface of the table. In this configuration, the tip (62) of the extended handle (56) of the Gasper speculum will contact the table surface and the tip (97) (78) of the dilation blades will be too far above the entrance of the vagina if the blades are held parallel to the table surface.

The locking mechanism in the Gasper design is such that when forward and upward or backward pressure is exerted on the upper blade (24) & (32), the locking tongue (44) will be dislodged from the slots (82) (84) (86), causing unintended closure of the blades (24) (50), resulting in possible entrapment of the vaginal wall and pain and discomfort to the patient. Such upward and forward movement is commonly encountered in the normal use of a speculum as the doctor attempts to introduce or withdraw instruments such as a sponge holding forceps between the opened blades (24) (50) and the problems referred to above are not uncommon. A locking mechanism is preferably steady and reliable so as not likely to be disengaged by accidental movement on any part of the device and with disengagement of the looking mechanism occurring only intentionally.

To insert the Gasper speculum, it is necessary to tilt the device to a degree that insertion and subsequent opening of the blades (24) (50) is difficult and can cause the patient great discomfort. To examine a patient with known speculums, it is necessary to have the patient supported on a special gynaecological examination table. When a patient lies on such a table, the buttocks are at the rear edge of the table and the ankles are supported on stirrups. This configuration has the effect of tilting the entrance of the vagina upwards as well as leaving plenty of vertical space in front of and below the entrance of the vagina in order that the long handle (56) (62) can be accommodated. Doctors without a gynaecological table find it difficult to use known speculums which have long handles with tips more than 8 om vertically from the horizontal blade surfaces.

U.S. Pat. No. 3,528,409 to Bruder also discloses a disposable speculum. This speculum has handle portions in substantial alignment with their respective blade portions. As these handles are also particulary short the device is difficult to use in a controlled and effective manner.

SUMMARY OF THE INVENTION

The present invention aims to alleviate the above disadvantages and to provide a vaginal speculum which will be reliable and efficient in use. Other objects and advantages of this invention will hereinafter become apparent.

With the foregoing and other objects in view, this invention in one aspect resides broadly in a vaginal speculum including:

a blade assembly having upper and lower pivotally interconnected elongate dilator blade members movable between a closed position at which the blade assembly extends along a longitudinal blade assembly axis and an open position at which said blades are spaced from said blade assembly axis, and a handle assembly having rearwardly extending handle members which incline downwardly from said blade assembly axis, said handle assembly being operable to move said blade assembly between said open and closed positions;

wherein the distance between said blade assembly axis and the lowermost portion of said handle assembly substantially corresponds to the distance between the vaginal entrance of a recumbent adult supported on a flat surface and said flat surface.

This distance will vary in accordance with the physical characteristics of the individual and of race. However whilst a minimum distance of separation is not required it is preferred that the distance of separation be less than 8 centimetres and is preferably between 4 and 6 centimeters.

The handle members may be connected to the blade members by suitable linkages such as will permit handle members to be held in an orientation varying from the plane of the blade members. Thus for example the arrangement could be such that when the handle assembly is gripped in a horizontal configuration, the blade members are positioned for movement in a vertical plane. Alternatively the handle members can be linked to the blade members so as to lie in the same plane as the blade members. In a preferred embodiment each handle member is integral with a blade member and can be formed by an extrusion or moulding process.

In a preferred embodiment looking means are to retain the dilator blades in either a closed position and in a plurality of open positions. The locking means could for example be a hasp and clasp arrangement, a frictionally activated device or a worm and screw mechanism. However it is preferred that the locking means includes fastening means on one handle member which is engageable with retaining means on the other handle member. Preferably the fastening means includes a ratchet member depending from the upper handle member and the retaining means comprises a slot in the lower handle member.

The speculum may be constructed of synthetic plastics material. The material may be a transparent material such as polymethyl methacrylate (perspex or lucite) or polystyrene so that the roof and floor of the vaginal wall are visible to the practitioner. Such a speculum may be disposable. Alternatively the synthetic material may be such as will enable the speculum to be sterilised for re-use. If desired, the dilator blades may be pre-coated with a suitable lubricant.

In another aspect this invention resides broadly in a vaginal speculum including:

a blade assembly having upper and lower pivotally interconnected elongate dilator blade members movable between a closed position at which the blade assembly extends along a longitudinal blade assembly axis and an open position at which said blades are spaced from said blade assembly axis, and a handle assembly including upper and lower rearwardly extending downwardly inclined handle members formed as extensions of said upper and lower blade members respectively, said lower handle member including a first elongate portion proximate said pivotal interconnection and inclined downwardly from said lower elongate dilator blade at a substantially obtuse angle and a second elongate portion inclined rearwardly from said first elongate portion and in substantially parallel alignment with said blade assembly axis, said handle assembly being operable to move said blade assembly between said open and closed positions;

Wherein the distance between said blade assembly axis and the lowermost portion of said handle assembly substantially corresponds to the distance between the vaginal entrance of a recumbent adult supported on a flat surface and said flat surface.

BRIEF DESCRIPTION OF THE DRAWINGS

In order that this invention may be more easily understood and put into practical effect, reference will now be made to the accompanying drawings which illustrate a preferred embodiment of the invention, wherein:

FIGS. 4 and 5 are front and rear elevations respectively;

FIG. 6 illustrates the usage of a known bi-valve speculum;

DETAILED DESCRIPTION OF THE DRAWINGS

Figure 1:
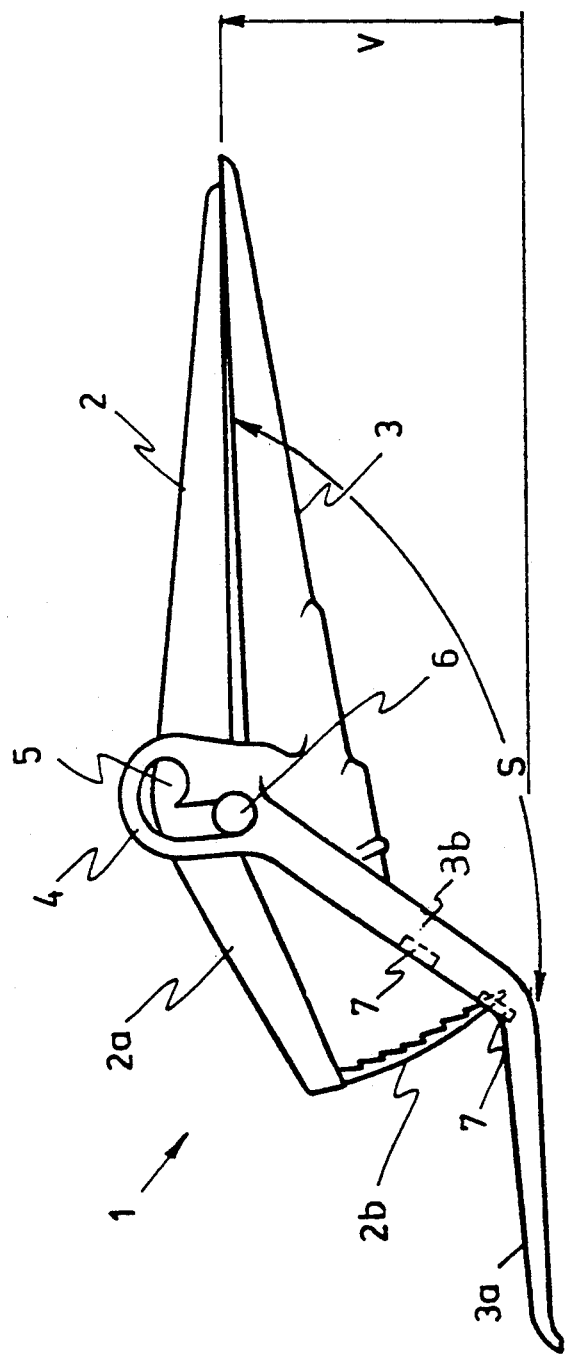
FIG. 1 is a side elevation of the speculum of the invention.
Figure 2:
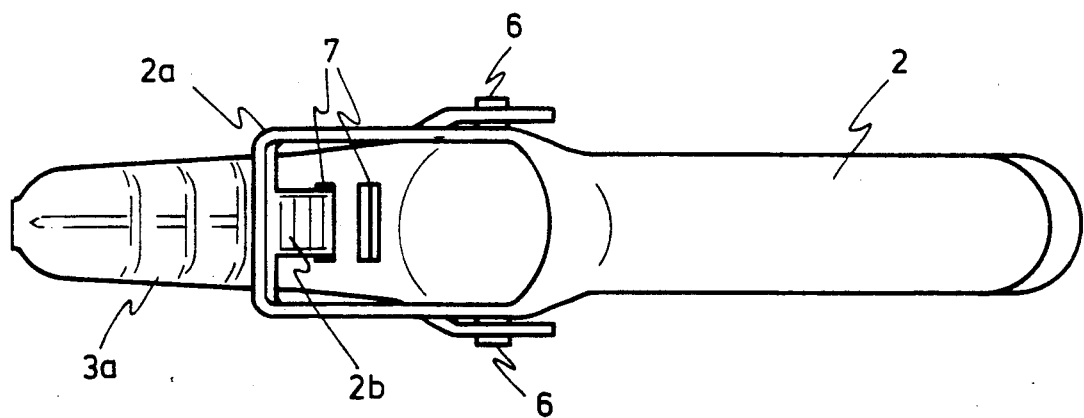
FIG. 2 is a plan view thereof.
Figure 3:
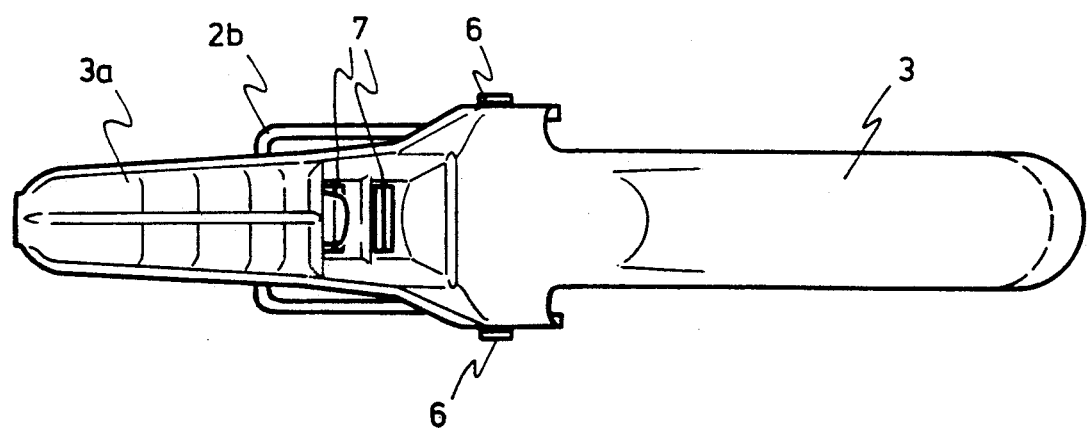
FIG. 3 is an underside (plan) view.

Referring to FIG. 1, a speculum 1 comprises dilator blades 2 and 3. Upper blade 2 has a rear extension 2a constituting a handle portion to which is attached downwardly depending ratchet member 2b. Lower blade 3 has a rear extension comprising two linear sections, 3a and 3b as shown. Section 3b includes a pair of slots 7 therein for receiving ratchet member 2b whereby to lock the positions of the blades 2 and 3 relative to each other. Blade 3 includes a pair of projections 4 each of which has a double slot 5 therein, for respectively receiving pivot pins 6 forming part of blade 2. Thus if pins 6 are in the rearmost slot, ratchet member 2b will engage in the rearmost of the two slots 7 as seen in FIG. 1, and if the pins are in the forward slot, ratchet member 2 engages in the foremost of the two slots 7. The fitting of pivot pins 6 in the longer end of slot 5 is such that no forward or rearward displacement is possible.

In operation, blades 2 and 3 (in closed position as shown in FIG. 1) are inserted into the patient's vagina. The practitioner grips section 3a which constitutes an elongate handle portion. Once the device is inserted, the practitioner presses handle portions 2a and 3b together, to spread the blades 2 and 3 and to engage the ratchet member 2b into one of slots 7, as appropriate. This distends the walls of the vagina so that they are more readily visible, and also makes visible the cervical area. It will be noted that the device is locked securely in this open position by the ratchet arrangement. The upwardly facing locking teeth of the ratchet 2b engage the upper surface of slot 7 thereby preventing the ratchet member 2b from sliding back and closing blades 2 and 3. The locking teeth are constrained into engagement with the upper surface of slot 7 by the tensile strength of the material of members 6, 2a, 2b and is not dependent on either gravitational force or the steady hand and grasp of the physician.

The angle between handle portion 3a and the median axis of the dilator blades (the angle S as seen in FIG. 1) is substantially between 170 and 180 degrees i.e. the two axis are almost parallel. The vertical distance between the upper horizontal surface of the lower blade and the lowermost portion of handle 3a (distance V as seen in FIG. 1) substantially corresponds to the distance between the vaginal entrance of a recumbent adult supported on a flat surface and the flat surface itself. This distance will vary in accordance with the physical characteristics of the individual and of race. However whilst a minimum distance of separation is not required it is preferred that the distance of separation be less than 8 centimetres. In the preferred embodiment illustrated the distance V is approximately 5.5 centimeters.

It is preferred that the spread between the tips of blade members 2 and 3 does not exceed 4 cm before the first notch of the ratchet mechanism is engaged in order to minimise discomfort to the patient. So that the locking mechanism is secure and failproof and so that unintended disengagement of the locking mechanism is not possible by any means other than the intended action by the practitioner, the locking tongue (2b) having upwardly facing looking teeth is inserted into the slot (7) and is automatically locked in place so as not to be disengaged by accidental upward, forward or backward pressure on the upper blade (2).

Figure 7:
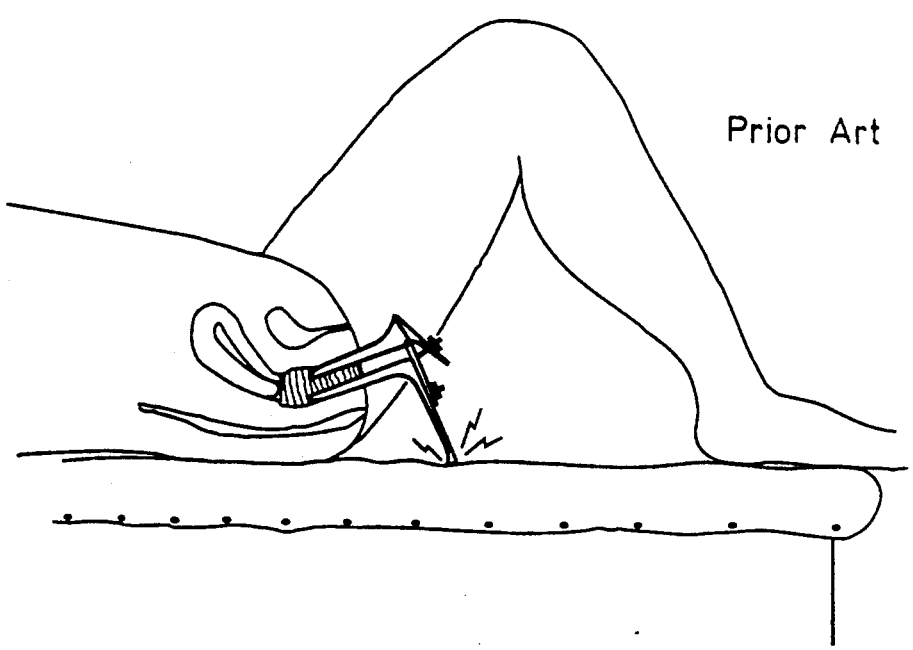
FIG. 7 illustrates a common problem with known bi-valve speculums.

FIG. 6 illustrates how conventional prior art speculums having a handle at right angles to the blades are suitable for examining patients supported on special gynascological examination tables which are infrequently found in the surgeries of general practitioners. As can be clearly seen in FIG. 7, conventional prior art speculums are unsuitable to use when examining patients on normal couches because the handle contacts the couch and prevents the speculum being properly inserted. The angle adopted by the blades during insertion results in excessive distension of the vagina.

Figure 8:
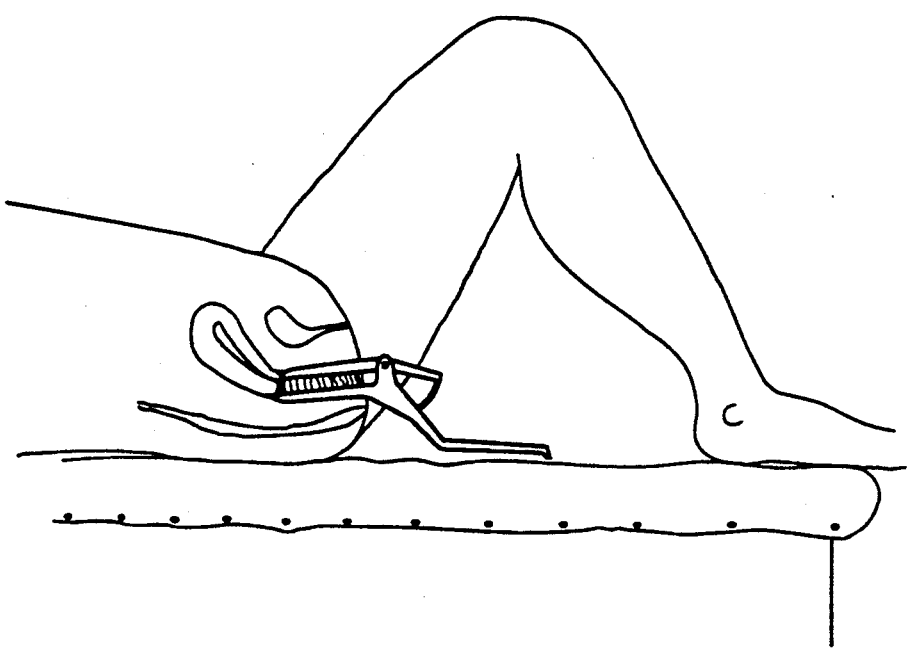
FIG. 8 illustrates use of the present invention on patients lying on ordinary flat examination tables.

As can be seen in FIG. 8, the speculum in accordance with this invention enables general practitioners without a gynaecological examination table to examine patients effectively and efficiently whilst causing minimum discomfort. This is of considerable benefit both to patients and general practitioners who collectively perform the majority of gynaecological screening tests such as Pap smears.

It will of course be realised that whilst the above has been given by way of an illustrative example of this invention, all such and other modifications and variations hereto, as would be apparent to persons skilled in the art, are deemed to fall within the broad scope and ambit of this invention as herein claimed.

I claim:

1. A vaginal speculum, comprising:
  a blade assembly having upper and lower pivotally interconnected elongate dilator blade members movable between a closed position at which the blade assembly extends along a longitudinal blade assembly axis and an open position at which said blades are spaced from said blade assembly axis; and,
  a handle assembly including upper and lower rearwardly extending and downwardly inclined handle members formed as extensions of said upper and lower blade members respectively, said lower handle member including a first elongate portion proximate said pivotal interconnection and inclined downwardly from said lower elongate dilator blade at a substantially obtuse angle and a second elongate portion inclined rearwardly from said first elongate portion and in substantially parallel alignment with said blade assembly axis, said handle assembly being operable to move said blade assembly between said open and closed positions.

2. The vaginal speculum according to claim 1, wherein when a recumbent adult female is supported on a flat surface and said blade assembly axis is substantially parallel to said flat surface and aligned with the vaginal entrance, the lowermost portion of said handle assembly is located above said flat surface.

3. The vaginal speculum according to claim 1, wherein the distance between said blade assembly axis and the lowermost portion of said handle assembly is less than 8 centimeters.

4. The vaginal speculum according to claim 3, wherein the distance between said blade assembly axis and the lowermost portion of said handle assembly is between 4 and 6 centimeters.

5. The vaginal speculum according to claim 1, further comprising locking means for retaining said dilator blades in said closed position or in a plurality of open positions.

6. The vaginal speculum according to claim 5, wherein said locking means includes fastening means on one of said handle members engageable with retaining means on the other said handle member.

7. The vaginal speculum according to claim 6, wherein said fastening means includes a ratchet member on said one handle member and wherein said retaining means comprises a slot in said other handle member through which said ratchet member is capable of passing.

8. The vaginal speculum according to claim 1, wherein said speculum is constructed of a synthetic plastic material.

9. The vaginal speculum according to claim 8, wherein said synthetic plastic material is polymethyl methacrylate.

* * * * *